US005914113A

United States Patent [19]

Schrier

[11] Patent Number: 5,914,113

[45] Date of Patent: Jun. 22, 1999

[54] INACTIVATED VACCINES

[75] Inventor: Carla Christina Schrier, Boxmeer, Netherlands

[73] Assignee: Akzo Nobel, N.V., Arnhem, Netherlands

[21] Appl. No.: 08/939,046

[22] Filed: Sep. 26, 1997

[30] Foreign Application Priority Data

Sep. 27, 1996 [EP] European Pat. Off. .............. 96202708

[51] Int. Cl.[6] ......................... A61K 39/295; A61K 39/12

[52] U.S. Cl. .................................... 424/201.1; 424/204.1; 424/816; 424/202.1; 435/235.1; 435/236

[58] Field of Search ............................. 424/199.1, 204.1, 424/201.1, 202.1, 816; 435/235.1, 236

[56] References Cited

U.S. PATENT DOCUMENTS

| | | | |
|---|---|---|---|
| 5,037,650 | 8/1991 | Schrier | 424/202.1 |
| 5,686,077 | 11/1997 | Schrier | 424/201.1 |
| 5,728,569 | 3/1998 | Schrier | 435/235.1 |
| 5,733,556 | 3/1998 | Schrier et al. | 424/214.1 |
| 5,750,111 | 5/1998 | Schrier | 424/214.1 |

FOREIGN PATENT DOCUMENTS

| | | |
|---|---|---|
| 0479627 | 4/1992 | European Pat. Off. . |
| 0533294 | 3/1993 | European Pat. Off. . |
| 1059095 | 2/1967 | United Kingdom . |
| 2170708 | 8/1986 | United Kingdom . |

OTHER PUBLICATIONS

Nishino et al. 1991, J. Gen. of Virology, vol. 72, pp. 1187–1190.

Immunology, 1980, Harper & Row Publisher, pp. 291–295.

*Primary Examiner*—Mary E. Mosher
*Assistant Examiner*—Ali R. Salimi
*Attorney, Agent, or Firm*—Mary E. Gormley

[57] ABSTRACT

The present invention is concerned with the preparation of improved inactivated vaccines, in particular of inactivated poultry vaccines. The immunogenicity of the inactivated immunogens in such vaccines is enhanced in case live CAV are administered in a combination vaccine with these inactivated immnogens.

17 Claims, No Drawings

INACTIVATED VACCINES

FIELD OF THE INVENTION

The present invention is concerned with a vaccine composition comprising one or more inactivated immunogens derived from avian pathogens and an adjuvant.

BACKGROUND OF THE INVENTION

Infectious diseases still afflict hundred of millions of mammalian and non-mammalian animal species, resulting in physical disabilities and death. In particular, the intensive method of raising animals for food under modern agricultural conditions make these animals extremely susceptible to these diseases. As a result, active immunization against the causative agents of these infectious diseases is required in order to reduce the economical losses associated with them. An ideal vaccine should elicit strong and long-lasting protective immunity with only a few injections, evoke minimal side-effects and should be safe. In the past many vaccines have been developed and successfully applied, although new outbreaks of diseases caused by new agents or by more virulent isolates of existing agents frequently occur. Vaccines can, in principle, be divided into two groups, i.e. live (attenuated) vaccines and inactivated vaccines. The advantages of live vaccines include the presentation of all the relevant immunogenic determinants of an infectious agent in its natural form to the host's immune system, and the necessity of a relatively small amount of the immunising agent, because of its inherent property to multiply in the vaccinated host. A major disadvantage of a live vaccine is concerned with its safety: a live vaccine may induce disease (in immuno-compromised) animals, or the live microorganism may even revert to virulence, as a result of which animals experience a virulent infection. Moreover, with respect to some infectious agents, until now, no attenuated forms of these agents are available.

The disadvantage concerning the safety aspect is not displayed by inactivated vaccines and, hence, constitutes the major advantage over live vaccines. However, a major disadvantage of inactivated vaccines is represented by their intrinsicly low immunogenicity, i.e. inactivated immunogens as such have a limited ability to trigger the host's immune system. Therefore, appropriate means are necessary to augment the immunogenicity of these inactivated immunogens. This type of vaccines normally requires adjuvants with significant immunostimulatory capabilities to reach a minimum potential in preventing disease. However, the desirability of additional immunostimulators for use in combination with inactivated immunogens in order to augment their inherently low immunogenicity is evident, in particular immunostimulators which are applicable to more than one immunogen.

In the field of poultry vaccines U.K. patent no. 2170708 (1986) discloses the preparation of a live vaccine comprising a live attenuated form of a poultry pathogen, such as Newcastle disease virus (NDV) and fowl-pox virus (FPV) which is mixed with a previously prepared water-in-oil (w/o) adjuvant emulsion containing no immunogens, in order to benefit from the advantages of both a live vaccine and a w/o emulsion adjuvanted inactivated vaccine.

European patent application no. 92202864.2 (publication no. EP 0533294), incorporated herein by reference, discloses a poultry vaccine for combating chicken anaemia virus (CAV) infection in poultry, the vaccine being based on an attenuated form of CAV. Furthermore, combination vaccines derived from this attenuated CAV and other poultry pathogens are disclosed.

SUMMARY OF THE INVENTION

It is an object of the present invention to provide improved inactivated vaccines, in particular inactivated avian vaccines. This object is met by the present invention by providing a vaccine composition comprising one or more inactivated immunogens derived from avian pathogens and an adjuvant, characterized in that the vaccine composition in addition comprises a live CAV immunogen. It has surprisingly been found that the immunogenicity of inactivated avian immunogens commonly present in commercially available inactivated poultry vaccines is potentiated by the combination with an immunogen, i.e. live CAV immunogen, unrelated to these former avian immunogens. Additionally, the live CAV immunogen component is also able to evoke a solid immune response in the new live/inactivated combination vaccine according to the present invention.

DETAILED DESCRIPTION OF THE INVENTION

The term "inactivated immunogens derived from avian pathogens" refers to immunogenic material derived from a microorganism infectious to avian species, in particular to poultry, which immunogenic material is non-replicative, as opposed to live immunogens. Inactivated immunogens include killed whole microorganism, extracts thereof or purified subunits (if desired produced by recombinant DNA techniques) of these microorganisms. The immunogens may be produced by methods known in the art or may be purchased from commercial sources.

Without limitations thereto, exemplary avian species include chickens, turkeys, geese, ducks, pheasants, pigeons, and the like. In particular this invention is applicable to chickens.

The advantages of this invention reside in the improved prevention of disease which threaten avians during their life. These avian diseases include any disease of viral, bacterial or other microbial origin. The examples demonstrate that live CAV immunogen is able to enhance the immunogenicity of unrelated inactivated avian immunogens significantly, or to evoke an earlier onset of immunity of inactivated immunogens, when these components are administered in combination.

Preferably, the vaccine composition according to the invention comprises inactivated immunogens derived from Newcastle disease virus (NDV), Infectious bronchitis virus (IBV), Infectious bursal disease virus (IBDV), Turkey rhinotracheitis virus (TRTV), Infectious laryngotracheitis virus (ILTV), Egg drop syndrome (EDS) virus, avian encephalomyelitis virus, reticuloendotheleisis virus, avian pox viruses, avian adenoviruses, infectious coryza, fowl typhoid, fowl cholera, *Mycoplasma gallisepticum, E. coli* and Salmonella.

More preferably, the inactivated immunogen(s) are derived from the group consisting of IBV, NDV and IBDV.

Although the vaccine composition according to the invention may comprise an inactivated immunogen derived from one type of avian pathogen, in order to provide a relief for the vaccination schedule for poultry, which is already mostly overloaded, resulting in a stress factor for the birds and an important cost factor for the farmers, a vaccine composition comprising two or more different inactivated immunogens is preferred.

The type of adjuvant to be used in the present invention is not critical as long it is able to increase an antigen-specific immune response of the inactivated immunogen(s). Such adjuvants are generally known in the art, and include oil-emulsions, aluminium salts or gels, such as aluminium hydroxide or-phosphate, saponins, polymers based on polyacrylic acid, such as carbopols, non-ionic block polymers, fatty acid amines, such as avridin and DDA, polymers based on dextran, such as dextran sulphate and DEAE dextran, biodegradable microcapsules, liposomes, bacterial immunestimulators, such as MDP and LPS, glucans and the like (see Altman and Dixon, Advances in Veterinary Science and Comparative Medicine, Vol. 33, 301–343, 1989).

The live CAV immunogen vaccine component comprises both live non-attenuated CAV (field) strains and live attenuated CAV strains. Because, chickens develop an age-dependent CAV resistance, which is completed at about two weeks of age, a vaccine according to the invention comprising a live non-attenuated CAV strain is administered usually to older animals, e.g. to breeders and layers 10–20 weeks of age.. An example of such a vaccine is described by von Bülow and Witt (J. Vet. Med. 33, 664–669, 1986).

Preferably, a vaccine according to the invention comprises a live attenuated CAV strain, because such a vaccine strain is safer in use, not only for the inoculated animals themselves, but also because such a vaccine reduces the possible adverse effects of spreading of the live vaccine strain to susceptible animals. Such a vaccine composition can be administered to both young and older birds. i.e. from one-day-old onwards. The preparation of live attenuated CAV vaccines is described in European patent application no. 92202864.2 (publication no. EP 0533294).

The preparation of a vaccine composition according to the invention will employ an effective amount of both the inactivated immunogen(s) and the live CAV immunogen, i.e. an amount of the immunogen that will cause the vaccinated animal to produce a specific and sufficient immune response to provide protection against subsequent exposure of a pathogen immunized against. The required effective amount of immunogen is dependent on the type of pathogen against which protection is sought, the type of the immunogen and the kind or age of the animal to be vaccinated. The determination of the required amount lies within the purview of the person skilled in the art.

The preparation of a vaccine composition according to the invention can by carried out using standard techniques. Both the preparation of the live CAV immunogen, the preparation of the inactivated immunogen(s) and the formulation of these components together with an adjuvant are conventional, and include the mixing of the live CAV immunogen with the inactivated immunogens(s) and the adjuvant. The preparation of vaccine compositions is inter alia described in "Handbuch der Schutzimpfungen in der Tiermedizin" (eds.: Mayr, A. et al., Verlag Paul Parey, Berlin und Hamburg, Germany, 1984) and "Vaccines for Veterinary Applications" (ed.:Peters, A. R. et al., Butterworth-Heinemann Ltd, 1993).

Preferably, the vaccine composition according to the present invention comprises an oil-emulsion as the adjuvant. Oil-emulsions are powerful immuno-stimulatory agents that have been used successfully as adjuvants in vaccines, especially in veterinary vaccines. An oil-emulsion to be used herein includes any water-in-oil (w/o) emulsion, oil-in-water (o/w) emulsion and w/o/w emulsion which can be administered to living animals without unacceptable side-effects. Usually, an oil-emulsion is composed of an aqueous phase, which can be made up of water, saline or a buffer (such as phosphate buffered saline), an oil phase and one or more emulsifiers, which components are extensively mixed by known techniques until a stable emulsion is obtained. As is well known in the art, the preparation of an o/w emulsion or a w/o emulsion, respectively, involves the appropriate choice of a suitable type of emulsifying agents, having regard to the relative proportions of the oil and water phases and their exact nature. The type of emulsion which the emulsifier is likely to promote is indicated by its relative affinity for oil and water, which is known as its hydrophylic-lipophilic balance (HLB). Generally, an emulsifier with an HLB of about 3–6 are required for the production of w/o-type emulsions. Suitable emulsifiers for o/w-type emulsions is usually found in the range of 10–18 (HLB). It is also general practice to combine two or more emulsifiers in such a way that a desired HLB value is obtained. In fact, this approach with a combination of emulsifiers usually leads to a more stable emulsion. Details concerning the production of pharmaceutical oil-emulsion can be found, for example in: "The Theory and Practice of Industrial Pharmacy" (eds.: Lachman, L. et al., Lea & Febiger, Philadelphia, U.S.A., 1970, Chapter 16), "Remington's Pharmaceutical Sciences" (ed.: Gennaro, A. R., Mack Publishing Company, Easton, U.S.A., 1990, 18th edition, "Bio-emulsifiers" , Zajic, J. E. et al. (in CRC Critical Reviews in microbiology, 1976, 19–66).

Examples of suitable oils include mineral oils, such as MARCOL, BAYOL and DRAKEOL, however, metabolizable oils are preferred. Although metabolizable oils are often found to be less potent adjuvants than mineral oils, the former have an important advantage in that they may cause less tissue reactions at the site of administration. An advantage of the present invention is that the positive effect of the live CAV immunogen on the immunogenicity of the inactivated immunogens in the vaccine composition allows the substitution of a mineral oil component of the emulsion by a metabolizable oil, without a concomitant reduction of the immunogenic potency of the inactivated immunogens, resulting in an efficacious vaccine composition which is more compatible with the tissue of the inoculated animal.

Any metabolizable oil, particularly from an animal, a fish or vegetable source may be used herein, if desired in refined or chemically modified form.

Examples of useful vegetable oils include peanut oil, soybean oil, coconut oil, olive oil, cotton seed oil, sunflower oil, sesame oil, and corn oil. Most fish contain metabolizable oils which maybe used herein, such as cod liver oil and shark liver oil. In addition, terpenoid derivatives from fish oils, such as squalene maybe readily used for the preparation of the oil-emulsion.

The oil component in the continuous phase of a w/o emulsion in a vaccine composition according to the present invention may constitute about 50–80% by weight, in particular 55–70% by weight of the vaccine composition. When the vaccine composition according to the present invention is based on an o/w emulsion, the continuous aqueous phase may constitute between 50–99% by weight, in particular between 75–95% by weight, of the vaccine composition.

Exemplary emulsifiers useful for carrying out the concept of this invention include emulsifiers from the following groups: fatty-acid substituted sorbitan surfactants, such as sorbitan monolaurate, -monopalmitate, -monoestearate, -monooleate etc. (commercially available under the name SPAN® and ARLACEL®) and a related group of surfactants comprising polyoxyethylene sorbitan monoesters and -triesters (commercially available under the name TWEEN®). More details concerning specific emulsifiers and the use thereof for the preparation of oil-emulsion based vaccines are described e.g. in International application WO 90/14837 and U.S. Pat. No. 3,919,411.

In a preferred vaccine composition according to the invention the oil-emulsion adjuvant is a w/o emulsion. In general, w/o type of emulsions are able to elicit a more potent immune response than vaccine compositions based on o/w emulsions. At present most inactivated poultry vaccines are based on w/o emulsions. Examples of commercially available inactivated poultry vaccines are mentioned below. In addition to the prior art documents mentioned in the previous paragraph, the preparation of inactivated vaccines based on w/o emulsions are also described in Altman and Dixon (1989, supra) and U.K. patent no. GB 2170708.

A vaccine composition according to the present invention may comprises the live CAV immunogen in an emulsified form together with the inactivated immunogen(s) in the w/o emulsion, the vaccine composition being a stable emulsion of all the immunogens in the w/o emulsion.

In a preferred embodiment of the invention, the live CAV immunogen is not simultaneously emulsified with the inactivated immunogens in the w/o emulsion, but is mixed subsequently with the w/o emulsion comprising the inactivated immunogens. This mixing involves only the input of low energy, for example manual shaking of the mixture, and does not require high energy input, such as high shear forces usually applied by conventional emulsification apparatus. The resulting vaccine composition comprises two phases: a first phase comprising the w/o emulsion and a second phase comprising the live CAV immunogen. In this vaccine composition the live CAV immunogen particles are not stably emulsified in the w/o emulsion, but only homogeneously distributed in the w/o emulsion (after mixing or shaking of the two phases).

Such a preferred vaccine composition can easily be prepared by combining the live CAV immunogen with the w/o emulsion comprising the inactivated immunogen(s), and subsequently mixing or shaking of the two phases, preferably this vaccine composition is prepared just prior to administration to the animals.

A vaccine composition according to the present invention can, for example, be obtained by combining a live CAV immunogen with inactivated poultry (combination) vaccines commercially available from veterinary vaccine suppliers. For example, inactivated poultry vaccines selected from the poultry vaccine range, commercially available from Intervet International B. V., the Netherlands can be used for the preparation of the present vaccine composition, e.g. NEWCAVAC NOBILIS, NOBI-VAC IB+ND, NOBI-VAC REO+ IB+G+ND, NOBI-VAC EDS'76, and NOBI-VAC IB3+G+ ND can be used for this purpose.

In case a vaccine composition according to the invention is contemplated which is instantly prepared just prior to its use, the live CAV immunogen is generally presented as a live culture of the virus, for example in a stabilized form, e.g. as a freeze-dried powder, together with conventional stabilizers.

In an even more preferred embodiment of the invention, said second phase comprises the live CAV immunogen dissolved in an aqueous solution. Such a vaccine composition is obtained by reconstituting the live (freeze-dried) CAV immunogen first in an aqueous solution, before the solution is combined with the w/o emulsion.

The vaccine composition according to the present invention based on an oil-emulsion may be produced by methods well known in the art for this purpose, such as described inter alia as described in the (handbook) documents mentioned-above.

In general, a method for the preparation of an oil-emulsion based vaccine composition according to the invention comprises the steps of: combining a live CAV immunogen and inactivated avian immunogen(s) with an oil, water and emulsifier and emulsifying the mixture, such that a stable emulsion is obtained. Alternatively, the live CAV immunogen is mixed with an established oil-emulsion, preferably a w/o emulsion, containing the inactivated immunogen(s).

The present invention is also concerned with a vaccine kit for the protection of avian species against infectious diseases, characterized in that the kit comprises a first container comprising the live CAV immunogen and a second container comprising an oil-emulsion containing the inactivated immunogen(s).

In a further preferred embodiment of the invention, the inactivated immunogen(s) are killed whole microorganisms, in particular killed whole viruses. The aim of providing killed microorganisms is to eliminate reproduction of the microorganisms after the propagation thereof in cell or tissue culture. In general, this can be achieved by chemical or physical means. Chemical inactivation can be effected by treating the microorganisms with, for example, enzymes, formaldehyde, β-propiolactone, ethylene-imine or a derivative thereof. If necessary, the inactivating compound is neutralised afterwards. Material inactivated with formaldehyde can, for example, be neutralised with thiosulphate. Physical inactivation can preferably be carried out by subjecting the microorganisms to energy-rich radiation, such as UV light, X-radiation or γ-radiation. If desired, the pH can be brought back to a value of about 7 after treatment.

Typically, the vaccine composition according to the invention comprises between $10^{20}$–$10^{7.0}$ tissue culture infectious dose$_{50}$ (TCID$_{50}$) per animal, preferably the dose ranges from $10^{3.0}$–$10^{5.0}$ TCID$_{50}$of the live CAV immunogen. The inactivated immunogens are usually present in the vaccine composition in an antigenic equivalent of $10^2$–$10^9$ ID$_{50}$ per dose, preferably between $10^3$–$10^7$ ID$_{50}$ per dose.

The vaccine composition according to the invention is usually administered parenterally, e.g. intramuscularly or subcutaneously.

In another aspect of the invention, a new use of live CAV immunogens is provided: from the examples it is made clear that live CAV immunogens potentiate the immunogenicity of unrelated inactivated immunogens. Therefore, the present invention provides a new use of live CAV immunogens as immunostimmulators in vaccines.

In still another aspect the invention provides the use of a live CAV for the manufacture of a vaccine for the protection of an animal against an infectious disease, said vaccine comprising inactivated immunogen(s) urelated to CAV, wherein the live CAV enhances the immunogenicity of said inactivated immunogen(s).

Of course this new use of live CAV immunogens is not limited to stimulating the immunogenicity of inactivated immunogens derived from avian pathogens, but said CAV immunogens can also be used to augment the immunogenicity of inactivated immunogens derived from non-avian pathogens in other animal species susceptible to CAV infection.

EXAMPLE 1

Combination vaccine comprising live CAV and inactivated reovirus+IBV+IBDV+NDV

Schedule of vaccination

At 3–4 weeks of age one group of 12 SPF chickens was inoculated with 0.5 ml of CAV vaccine NOBILIS® mixed in NOBI-VAC REO+IB+G+ND® comprising a mineral oil w/o emulsion, via the subcutaneous route; chickens in the second group (12 SPF chickens) were inoculated with 0.5 ml of NOBI-VAC Reo+IB+G+ND via the subcutaneous route. Both vaccines are commercially available from Intervet International B. V., the Netherlands.

Before inoculation and at 21, 28 and 42 days post inoculation blood samples were collected from all chickens individually.

Dose and dosing volume administered

The combination vaccine was prepared as follows: 500 ml of the commercially available inactivated poultry vaccine was thoroughly mixed with 1 ml of the commercially available live CAV vaccine. Prior to the addition to the inactivated Nobi-vac® vaccine the freeze-dried CAV was dissolved in PBS.

Chickens were treated as follows:

Group 1: 4.0 $\log_{10}$ $TCID_{50}$ of CAV per dose in Nobi-vac Reo+IB+G+ND® via the subcutaneous route (0.5 ml/animal)

Group 2: one dose of Nobi-vac Reo+IB+G+ND® via subcutaneous route (0.5 ml/animal)

Serology

At the start of the experiment and at 21, 28 and 42 days post inoculation blood samples were collected from all chickens individually from the wing-vein according to standard procedures.

Serum samples were examined for the absence/presence of antibodies to CAV in the CAV-Elisa test.

Additionally, serum samples were examined for the absence/presence of antibodies to NDV in the NDV hemagglutination inhibition test, of antibodies to IBDV in the IBDV virus neutralisation test, of antibodies to IBV in the IBV haem-agglutination inhibition test and of antibodies to Reo in the Reo-Elisa, all according to the standard procedures.

The results of these experiments are depicted in Table 1A and 1B below. The experiments show that the NDV antibody response in the presence of live CAV viruses is about 3 times higher than without the live CAV addition. In the case of IBV, the antibody response is about 16 times higher. For IBDV the improved immunogenicity can be identified in that an effective immune response is triggered earlier after vaccination, when the live CAV viruses are administered in the combination vaccine.

TABLE 1A

| | $\text{Log}_2$ CAV antibody titre at weeks post vaccination | | | | $\text{Log}_2$ NDV antibody titre at weeks post vaccination | | | | $\text{Log}_2$ Reo antibody titre at weeks post vaccination | | | |
|---|---|---|---|---|---|---|---|---|---|---|---|---|
| Group | 0 | 3 | 4 | 6 | 0 | 3 | 4 | 6 | 0 | 3 | 4 | 6 |
| 1 | 3.0 | 10.8 | 10.2 | 11.3 | 0.0 | 7.3 | 6.8 | 7.3 | neg | 15.3 | 15.7 | 15.2 |
| 2 | 3.0 | 3.0 | 3.0 | 3.0 | 0.0 | 6.2 | 5.4 | 6.0 | neg | 14.1 | 15.3 | 15.3 |

TABLE 1B

| | $\text{Log}_2$ IBV antibody titre at weeks post vaccination | | | | $\text{Log}_2$ IBDV antibody titre at weeks post vaccination | | | |
|---|---|---|---|---|---|---|---|---|
| Group | 0 | 3 | 4 | 6 | 0 | 3 | 4 | 6 |
| 1 | 3.0 | 4.8 | 7.4 | 8.6 | 0.0 | 15.8 | 15.8 | 15.3 |
| 2 | 3.3 | 3.1 | 3.6 | 4.7 | 0.0 | 13.3 | 16.3 | 14.7 |

I claim:

1. A vaccine composition comprising one or more inactivated immunogens derived from avian pathogens, an adjuvant, and a live chicken anemia virus (CAV) immunogen.

2. The vaccine composition according to claim 1, wherein the adjuvant is an oil-emulsion and the one or more inactivated immunogens are emulsified therein.

3. The vaccine composition according to claim 2, wherein the adjuvant is a water-in-oil (w/o) emulsion.

4. The vaccine composition according to claim 3, wherein the w/o emulsion constitutes a first phase and the live CAV immunogen constitutes a second phase of the vaccine composition.

5. The vaccine composition according to claim 4, wherein the second phase comprises an aqueous solution of the live CAV immunogen.

6. The vaccine composition according to claim 2, wherein the oil is a metabolizable oil.

7. The vaccine according to claim 3, wherein the oil is a metabolizable oil.

8. The vaccine according to claim 4, wherein the oil is a metabolizable oil.

9. The vaccine according to claim 5, wherein the oil is a metabolizable oil.

10. The vaccine composition according to claim 1, wherein the one or more inactivated immunogens are one or more killed whole microorganisms.

11. The vaccine according to claim 1, wherein the one or more inactivated immunogens are inactivated whole viruses.

12. The method of according to claim 1, wherein the live CAV immunogen is a live, attenuated CAV.

13. A method of immunizing avian species against infectious diseases, comprising administering the vaccine of claim 1 to the birds.

14. The method of claim 13, wherein the vaccine is administered parenterally.

15. The vaccine composition according to claim 1, wherein the one or more inactivated immunogens of the avian pathogens are derived from poultry pathogens selected from the group consisting of Newcastle disease virus (NDV), Infectious bronchitis virus (IBV), Infectious bursal disease virus (IBDV), Turkey rhinotracheitis virus (TRTV), Infectious laryngotracheitis virus (ILTV), Egg drop syndrome (EDS) virus, avian encephalomyelitis virus, reticuloendotheleisis virus, avian pox viruses, avian adenoviruses, infectious coryza, fowl typhoid, fowl cholera, *Mycoplasma gallisepticum. E. coli* and Salmonella.

16. The vaccine composition according to claim 8, wherein the inactivated immunogens of the avian pathogens are derived from poultry pathogens selected from the group consisting of IBV, NDV and IBDV.

17. A vaccine kit for the protection of avian species against infectious diseases, comprising a first container comprising a live CAV immunogen and a second container comprising an oil-emulsion containing one or more inactivated immunogens derived from poultry pathogens.

* * * * *

UNITED STATES PATENT AND TRADEMARK OFFICE

CERTIFICATE OF CORRECTION

PATENT NO. : 5,914,113

DATED : June 22, 1999

INVENTOR(S) : SCHRIER

It is certified that error appears in the above-identified patent and that said Letters Patent is hereby corrected as shown below:

correct line 1 of claim 12 by changing "method" to -- vaccine --.

Signed and Sealed this

Fifth Day of September, 2000

Attest:

Q. TODD DICKINSON

*Attesting Officer*

*Director of Patents and Trademarks*